United States Patent
Roger et al.

(10) Patent No.: US 7,995,816 B2
(45) Date of Patent: Aug. 9, 2011

(54) DETECTING ACCESS DISCONNECT BY PATTERN RECOGNITION

(75) Inventors: Rodolfo G. Roger, Clearwater, FL (US); Atif Yardimci, Vernon Hills, IL (US)

(73) Assignees: Baxter International Inc., Deerfield, IL (US); Baxter Healthcare S.A., Glattpark (Opfikon) (CH)

(*) Notice: Subject to any disclaimer, the term of this patent is extended or adjusted under 35 U.S.C. 154(b) by 988 days.

(21) Appl. No.: 11/860,061

(22) Filed: Sep. 24, 2007

(65) Prior Publication Data
US 2009/0080757 A1   Mar. 26, 2009

(51) Int. Cl.
G06K 9/00   (2006.01)
(52) U.S. Cl. .......................... 382/128; 382/181
(58) Field of Classification Search ........... 382/128
See application file for complete search history.

(56) References Cited

U.S. PATENT DOCUMENTS

| | | | |
|---|---|---|---|
| 4,294,513 A | 10/1981 | Nelson et al. | |
| 4,342,907 A | 8/1982 | Macedo et al. | |
| 4,369,525 A | 1/1983 | Breton et al. | |
| 4,733,068 A | 3/1988 | Thiele et al. | |
| 5,741,213 A * | 4/1998 | Kouchi et al. | 600/310 |
| 5,901,978 A | 5/1999 | Breed et al. | |
| 5,917,180 A | 6/1999 | Reimer et al. | |
| 5,987,346 A * | 11/1999 | Benaron et al. | 600/407 |
| 5,988,676 A | 11/1999 | Lotito et al. | |
| 6,040,532 A | 3/2000 | Munch | |
| 6,127,672 A | 10/2000 | Danisch | |
| 6,173,068 B1 * | 1/2001 | Prokoski | 382/115 |
| 6,230,046 B1 * | 5/2001 | Crane et al. | 600/476 |
| 6,353,394 B1 | 3/2002 | Maeda et al. | |
| 6,397,136 B1 | 5/2002 | Breed et al. | |
| 6,422,545 B1 | 7/2002 | Baudendistel et al. | |
| 6,582,370 B2 * | 6/2003 | Jibiki | 600/455 |
| 6,845,339 B2 | 1/2005 | Winkler et al. | |
| 6,993,167 B1 * | 1/2006 | Skladnev et al. | 382/128 |
| 7,043,997 B2 | 5/2006 | Mattson et al. | |
| 7,248,724 B2 * | 7/2007 | Gutenev | 382/128 |

(Continued)

FOREIGN PATENT DOCUMENTS
DE   4014572   5/1990
(Continued)

OTHER PUBLICATIONS

International Search Report for PCT/US2008/066079 filed Jun. 6, 2008 mailed Feb. 17, 2009.
(Continued)

*Primary Examiner* — Sath V Perungavoor
(74) *Attorney, Agent, or Firm* — K&L Gates LLP (57) ABSTRACT

A blood detection system is used to detect blood in a patient undergoing an extracorporeal blood therapy, such as hemodialysis or apheresis. The blood detection system uses a digital video device, which may be a camera, such as a standard digital video camera, a low light camera, an infrared camera, or a night vision camera. The digital image is sent to a computer with image processing and pattern recognition software. The software is used to detect whether a pool of blood is forming at the access site. The system is able to detect a pool of blood atop the access site, such as when a leak or a dislodgement of a needle occurs. The system is also able to detect pooling of blood under the skin, as a result, for instance, infiltration of an arteriovenous fistula.

24 Claims, 6 Drawing Sheets

U.S. PATENT DOCUMENTS

| | | | |
|---|---|---|---|
| 7,792,334 B2 * | 9/2010 | Cohen et al. | 382/115 |
| 7,862,512 B2 * | 1/2011 | Iikubo et al. | 600/459 |
| 7,916,910 B2 * | 3/2011 | Cotton et al. | 382/128 |
| 2002/0136435 A1 * | 9/2002 | Prokoski | 382/118 |
| 2003/0128126 A1 * | 7/2003 | Burbank et al. | 340/605 |
| 2004/0122719 A1 * | 6/2004 | Sabol et al. | 705/7 |
| 2004/0122787 A1 * | 6/2004 | Avinash et al. | 706/50 |
| 2004/0122790 A1 * | 6/2004 | Walker et al. | 707/1 |
| 2004/0136579 A1 * | 7/2004 | Gutenev | 382/128 |
| 2004/0243048 A1 * | 12/2004 | Brugger et al. | 604/4.01 |
| 2004/0243049 A1 * | 12/2004 | Brugger et al. | 604/4.01 |
| 2004/0267102 A1 * | 12/2004 | Skladnev et al. | 600/315 |
| 2005/0157939 A1 * | 7/2005 | Arsenault et al. | 382/260 |
| 2006/0173351 A1 * | 8/2006 | Marcotte et al. | 600/473 |
| 2007/0049832 A1 * | 3/2007 | Edgar et al. | 600/476 |
| 2008/0075340 A1 * | 3/2008 | Cotton et al. | 382/128 |
| 2008/0218732 A1 * | 9/2008 | Mil'shtein et al. | 356/51 |
| 2009/0080757 A1 * | 3/2009 | Roger et al. | 382/134 |
| 2010/0087770 A1 * | 4/2010 | Bock et al. | 604/4.01 |

FOREIGN PATENT DOCUMENTS

| | | |
|---|---|---|
| EP | 1892001 | 8/2006 |
| FR | 2737124 | 1/1997 |

OTHER PUBLICATIONS

Written Opinion of the International Searching Authority for PCT/US2008/066079 mailed Feb. 17, 2009.

\* cited by examiner

DETECTING ACCESS DISCONNECT BY PATTERN RECOGNITION

BACKGROUND

The invention is in the field of medical treatments generally and patient vascular access systems. The present invention relates to embodiments of a method and a system for detecting blood leakage or infiltration during extracorporeal blood treatment or other medical procedure.

The maxim of "first, do no harm," may be a good summary of the Hippocratic oath required of doctors and practiced by medical professionals. Nowhere is this principle required more than in modern medicine. With patients living longer, there are more extended treatments and more frail patients than ever. Such patients are in danger from a number of complications that can arise from continuing therapeutic procedures, and even from diagnostic procedures, that are necessary for their continued care. Treatments involving extracorporeal blood treatment are clear examples.

The most obvious danger is infection, but the harm caused by infection can be overcome by not re-using even supposedly-sterile devices and by diligent attention by the patient himself or herself, and by care givers attending to the patient. Other dangers also arise, but, like infections, have been difficult to eradicate. One of these dangers arises in blood treatment procedures in which the blood of a patient is physically removed from the patient for treatment, and then returned, all in the same procedure. Removal and return of blood is practiced in hemodialysis, for those persons whose kidneys do not function well. Other procedures, such as apheresis, involve removing blood from a patient or a donor to separate blood platelets or plasma from the red blood cells and then returning the red blood cells to the patient or donor, as described in U.S. Pat. Nos. 5,427,695 and 6,071,421.

The extracorporeal medical treatments described above require that the blood be removed for treatment and then returned. This requires access to the patient's vascular system, from which blood is removed and to which blood is then returned. If a "batch" treatment is used, that is, a quantity of blood is withdrawn, treated and returned, only a single needle is used. Each batch of such treatment is typically short, and the treatment is attended by a medical professional at a clinic or hospital. A variation on the batch treatment is a "batch" continuous method in which only a single needle is used. There are distinct withdraw and return phases in a batch continuous process. During the draw phase, blood is processed and additional blood is sent to a holding container to be processed during the return phase. In the return phase, blood is processed from the holding container and then returned to the patient or donor through the single needle.

Other treatments are continuous, such as the platelet separation discussed above, or dialysis treatment, and may require a duration of several hours or even overnight.

Continuous treatments require two needles, or access points, one for withdrawal of blood and one for return. The withdrawal site is normally an artery, and a needle and a pump are used to provide the blood to the therapeutic machine. It is relatively simple to detect a problem with withdrawal, for instance, if the withdrawal needle is dislodged, using conventional air sensor technology. Detecting a problem in the return of the blood to the patient is more difficult. The return line typically includes a needle with venous access. If the return line is dislodged, the blood is not returned to the patient's vascular system, but may continue to be pumped and may accumulate near the patient. Depending on the pumping rate of the blood and the time for treatment, this could have life-threatening effects on the patient within a very short period of time.

Accordingly, a number of apparatuses have been devised for detecting needle dislodgement, especially venous needle dislodgement. An example is U.S. Pat. Appl. Publ. 2006/0130591. In a device according to this application, a venous needle is equipped with a photosensor and is covered with an opaque patch. This device would not send a signal or an alarm if the needle begins leaking or is only slightly dislodged. In this example, the photosensor could still fail to detect light because the needle has not been dislodged sufficiently to expose the photosensor to light. In addition, this method requires ambient light and would thus not be suitable for patients that cover their arm with a blanket or who perform nocturnal dialysis while sleeping in a dark bedroom.

Numerous other techniques have been devised, many of them depending on a flow of blood causing conductivity between two electrodes or two wires. What is needed is a better way of quickly detecting dislodgement of a venous or other needle from a patient, so that inadvertent loss of blood and harm to the patient is avoided.

Another complication that may arise during extracorporeal treatments or during infusion of intravenous medication is infiltration (internal leakage), in which vessel walls are compromised (usually through a double puncture by the needle through the target vessel), and blood leaks internally to the surrounding tissue. A reliable way to detect infiltration is also needed.

SUMMARY

One embodiment is a method of detecting blood leakage. The method includes steps of providing a digital video camera, mounting the camera to observe an extracorporeal blood processing access site, taking a baseline image of the access site on a patient, processing the baseline image with image processing software and saving data of the baseline image, monitoring the access site by taking additional images of the access site during an extracorporeal blood processing therapy and processing the additional images with the pattern recognition software, and sending a signal if a pattern of blood is detected.

Another embodiment is a method for detecting blood leakage at an access site. The method includes steps of providing a digital video device, mounting the device in viewing range of the access site on a patient, taking a baseline image of the access site, processing the baseline image with pattern recognition software, saving data of the baseline image, monitoring the access site during a therapy procedure by taking additional images and processing the additional images with the pattern recognition software, and sending a signal if a pattern indicative of a blood leak or infiltration is detected.

Another embodiment is a system for detecting blood leakage. The system includes a digital video device suitable for mounting near an access site for extracorporeal therapeutic blood processing, signal processing circuitry operably connected to the digital video device, image processing software on a computer readable medium operably connected to the signal processing circuitry, the image processing software suitable for recognizing a pattern, a microcontroller in communication with the digital video device and the circuitry, and a communications circuit in communication with the microcontroller, wherein the digital video device is configured for monitoring the access site during an extracorporeal blood processing therapy and for sending images of the site to the signal processing circuitry, and wherein the image processing software is configured to detect a leakage of blood or infiltration of blood by recognizing a pattern or shape during the therapy.

Another embodiment is a hemodialysis machine. The hemodialysis machine includes a machine for administering extracorporeal hemodialysis of blood of a patient and a system for detecting blood leakage during hemodialysis, the system operably connected to the machine. The system for detecting blood leakage further includes a digital video camera for monitoring an access site of the patient, signal processing circuitry for receiving signal data from the camera, image processing software on a computer readable medium operably connected to the signal processing circuitry, a microcontroller in communication with the digital video device and the circuitry, and a communications circuit in communication with the microcontroller, wherein the digital video device is configured for monitoring the access site during an extracorporeal blood processing therapy and for sending images of the site to the signal processing circuitry, and wherein the image processing software is configured to detect a leakage of blood or infiltration of blood that is growing during the therapy.

Additional features and advantages are described herein, and will be apparent from, the following Detailed Description and the figures.

DETAILED DESCRIPTION

Persons undergoing hemodialysis could lose very large quantities of blood if for any reason the return needle becomes dislodged. Blood has optical properties, such as absorbance and reflectance, that are very different from the normal properties of the surrounding tissue or access site. In particular, flesh of all people has a color that is distinct and different from that of blood, which normally has a red color. A fistula dialysis access site, or other access site, such as one for blood processing, will frequently be covered or protected with white gauze. If blood leaks from the site, the gauze will absorb the blood and the gauze color will change. Another problem that can occur with hemodialysis, as well as other treatments, is infiltration of the needle through the vein used for the arteriovenous fistula. In this case, infiltration results blood leaking internally within the person, under the skin. This leads to discoloration and may be immediately discernable upon inspection. Thus, ordinary, digital color cameras may be used to detect blood. Other cameras may also be used, such as infrared or thermal imaging cameras, as well as ultra low light, or night vision cameras.

A camera with color capabilities may be optimized for detecting blood by taking advantage of the ability of blood to absorb light of lower wavelengths, such as light with wavelengths between about 405 nm and about 532 nm. Thus, if there is a decrease of light at these wavelengths that is detected by a camera, this may be an indication of the presence of blood. On the contrary side, blood tends to reflect light at higher wavelengths, such as light having a wavelength of greater than 600 nm, such as about 800 nm. Thus, an increase in detection of light of over 600 nm, such as 800 mm, may indicate a presence of blood.

Blood is most easily detected at light with a wavelength of about 425 nm, a purplish color. This wavelength occurs at the isosbestic point of blood, that is, the point at which oxygenated and non-oxygenated blood absorb light about equally. This is a very good wavelength for detecting blood, because light at 425 nm will be selectively absorbed and detectors will note a decrease in the amount of available light of this wavelength. This wavelength is also important because it has a local maximum for the spectral absorbance of hemoglobin, that is, this is a wavelength at which an optical sensor would be maximally sensitive to the presence of hemoglobin. Thus, a video camera may easily detect blood if it is looking for a pattern with about this color. Alternately, the video camera could detect a growing pattern, as in a pool of blood, especially a pattern that is the color of blood. This would also apply to infiltration of the arteriovenous fistula, when the pool of blood is under the skin, but still very noticeable and its purplish color very distinct and different from that of normal flesh.

An infrared camera may also be used to detect venous disconnect. Infrared cameras detect light in the infrared range, higher wavelengths, that is, they detect heat. Thus, infrared cameras may be used to detect heat and differences in heat. Infrared cameras and thermal imaging are used to locate overheating joints and parts as an indication of potential failure. These applications are used with rotating equipment, electrical power lines, and many other applications. Faults in the thermal insulation can be detected by infrared emissions in building inspections. Firefighters use them to see through smoke to find persons and hot spots. Images from infrared cameras are in essence monochromatic but they can be mapped to a pseudo-color pattern where each color represents a different range of temperatures. The infrared imaging methods would be well suited for infiltration detection as well, as the tissue within the infiltration zone will be actively perfused with the blood coming from the vessel. This perfusion is also expected to lead to higher temperatures that would be picked up by the infrared imaging tools.

Night vision cameras or low light cameras may also be used. These cameras work by amplifying the available light using photomultipliers, micro-channel plates, or other amplification techniques. While more expensive than other options, they may also be used to detect blood.

Figure 1:
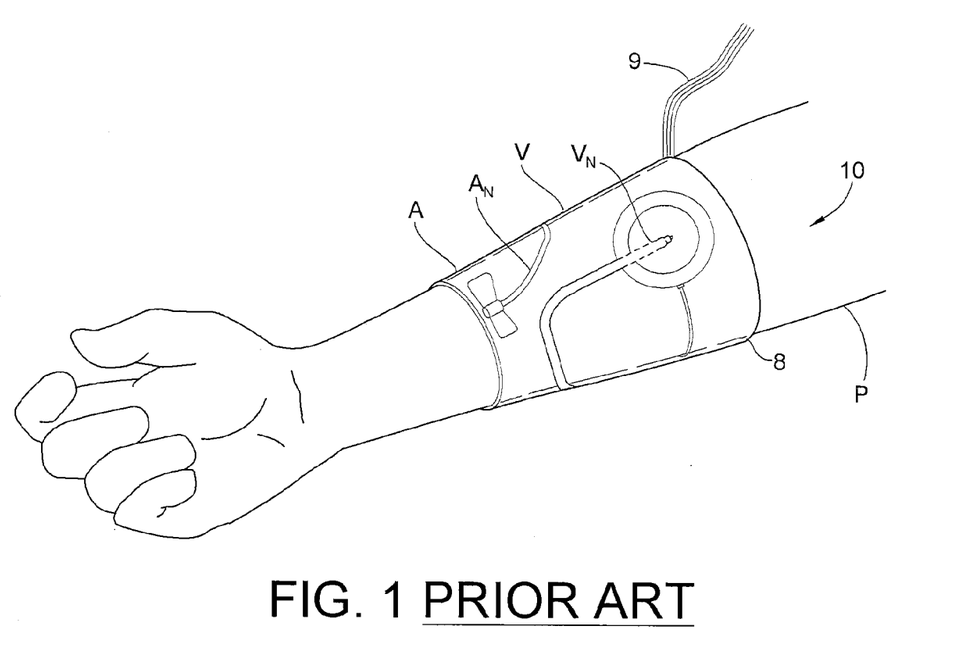
FIG. 1 is a perspective prior art view of a venous access site.
Figure 2A:
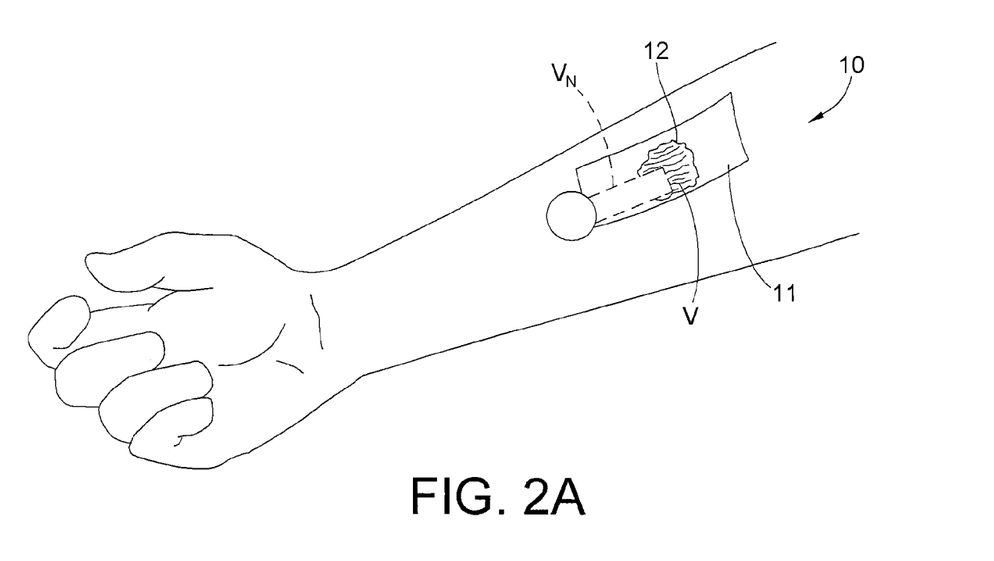
FIG. 2a is a plan view of a venous access site with in which venous access needle disconnect has occurred.
Figure 2B:
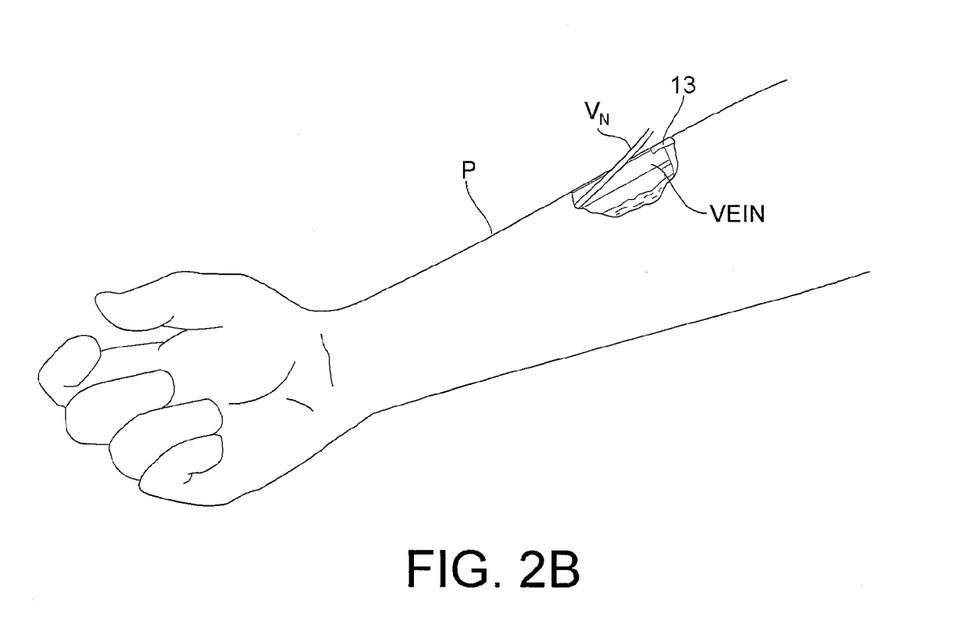
FIG. 2b is an elevational view of a venous access in which infiltration has occurred.
Figure 3:
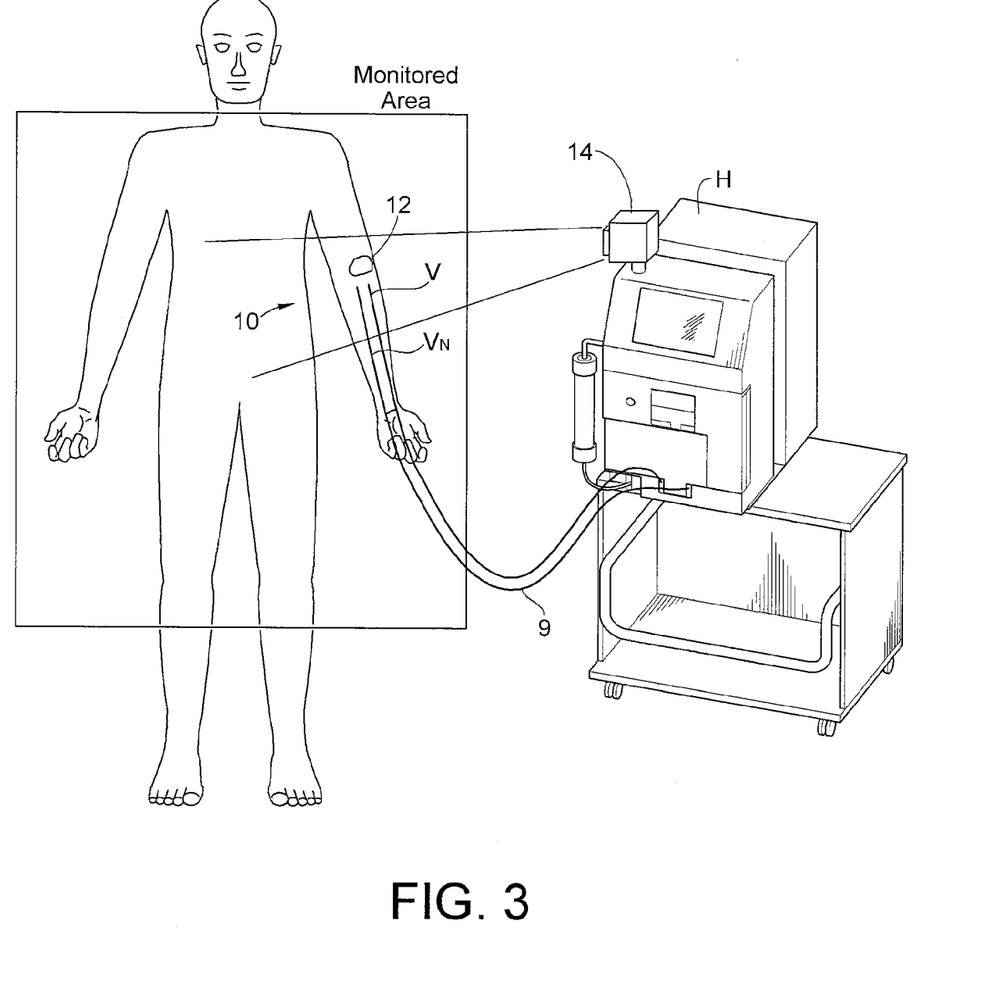
FIG. 3 is a schematic view of a first embodiment.

FIG. 1 depicts a patient P undergoing hemodialysis, with an access site 10 that includes an arterial access site A with an arterial needle $A_n$, venous access site V with a venous needle $V_n$, and a securing patch 8. Tubing 9 connects the patient to a nearby hemodialysis machine H (FIG. 3). FIGS. 2A and 2B depict the situation addressed in this patent by the embodiments disclosed. FIG. 2A depicts blood resulting from leakage at the fistula or from dislodgement of the venous needle $V_n$. At access site 10, covered by gauze or other absorbent, soft material 11, a pool 12 of blood has formed as a result of leakage or dislodgement. FIG. 2B depicts infiltration of needle $V_n$ through the vein, forming an infiltration zone and a pool 13 of blood under the skin of the patient P.

FIG. 3 depicts one embodiment in which a video camera 14 is mounted on or near the hemodialysis machine H to monitor the appropriate area near the access site 10, including venous access site V and needle $V_n$. In this figure, the access site is connected to the hemodialysis machine via blood tubing 9. Blood 12 is visible to an observer and to camera 14.

Figure 4:
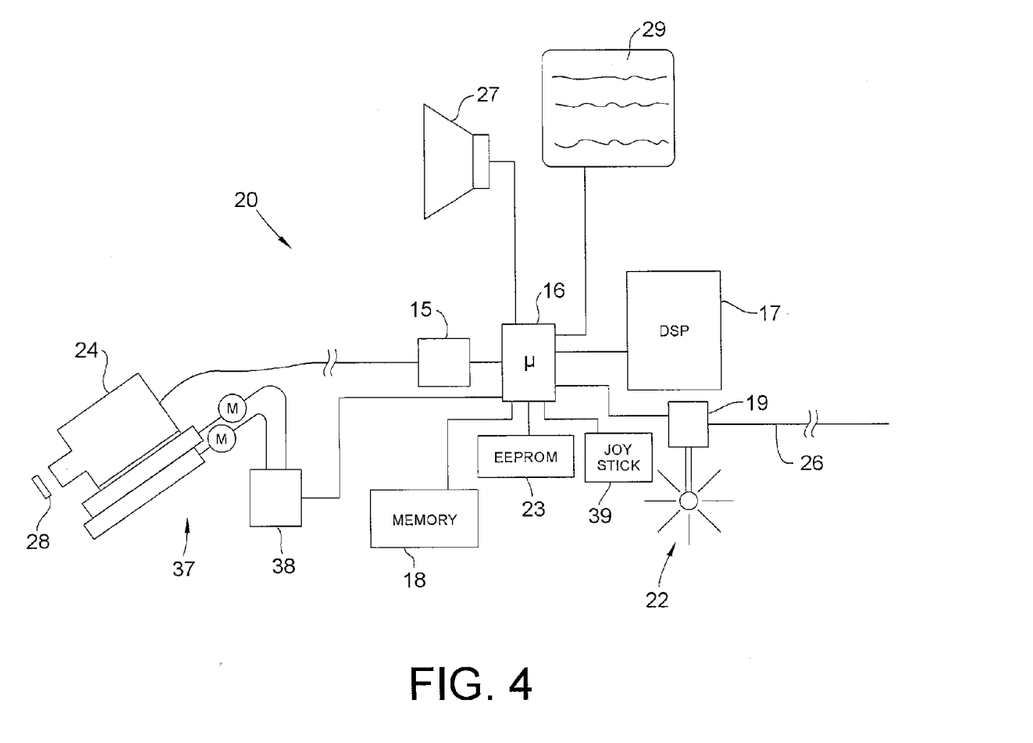
FIG. 4 is a schematic view of another embodiment.

A video camera may be used as part of an imaging and detection system 20 for detecting blood in the above-mentioned situations, as depicted in FIG. 4. In one embodiment, digital video device or camera 24 is mounted near the patient. If the patient is recumbent, the camera may be positioned above the patient, while for a sitting patient, the camera may be positioned near the side of the patient. A lens 28, described below, may be used to filter light received by the camera. Filtering may also be performed electronically. Camera 24 is connected to a system controller, including the components depicted. The camera itself is digital and includes circuitry sufficient to generate a signal that is useful for the detection system. The signal is typically analog and is converted to digital, typically using a multiplexer, an analog-to-digital converter, an amplifier, and other circuitry as necessary.

Multispectral imaging is available in some embodiments of the video system. This is the ability to generate multiple images separated by wavelength intervals, as done in earth-monitoring satellite imaging system, such as LANDSAT. The resulting multiple images can be used to differentiate and isolate detection of the areas of interest, an external blood leak or an internal infiltration. Many visualization operations may be performed on these multiple images. These operations, on the same domain, include differentiating infrared images from visible images and include custom matrix manipulations on the image. These include inversion, scalar/vector multiplication, and decomposition.

The camera or digital video device may be a charge-coupled device, a sensor array, or other optical device for receiving light and converting the light into a signal. A digital video device includes a plurality of picture elements, or pixels, each of which is part of the "image" that is taken. The device takes an image by periodically querying the pixels for their output, sending the output to a multiplexer, and then to data converters, typically at least one analog-to-digital converter, and then to memory or to signal processing circuitry.

The signal is relayed to an interface 15, which may be an amplifier or other circuitry necessary to receive the signal. Other components include a microcontroller 16, a digital signal processor (DSP) 17, memory 18, and a communications module 19. The communications module includes circuits necessary to send a signal, such as an alert or an alarm, locally or to a hospital information system or other outside receiver, wirelessly through antenna 22 or wired communication link 26.

Imaging and detection system 20 also includes an EEPROM 23. The system also includes local output devices, such as speaker 27 or video screen 29, either of which may be used to give an alarm or sound an alert. The camera may be mounted on a tilt and pan mechanism 37 controlled by a movement controller 38 in communication with microcontroller 16. Movement of the camera may be controlled by a keyboard or by a joystick 39 also in communication with the microcontroller 16 or movement controller 38.

EEPROM 23 may be used to store information that is used by the microprocessor or the DSP, but which may change and which can be re-programmed more easily than the microprocessor or the DSP. The EEPROM may be used to store calibration information for the digital video device or its circuitry. The EEPROM may also be used to store calibration values for light detection circuits, such as the sensor arrays mentioned above. It may also store error codes or diagnostic trouble codes as part of a built-in-test system that is part of the system for detecting blood or for administering hemodialysis. Such programs will store an error code for faults detected during run time for later interrogation and output. The EEPROM may also be used for storing calibration values useful for machine vision programs described below, and also for programs useful for calculating an area of a first or second pool of blood.

Programs that are useful for interpreting images taken by the camera or digital video device include machine vision image analysis programs, including programs for object segmentation and recognition. Once the signals are converted into digital signals, the signals may be processed by a host of techniques that are well known. These include adjustment of images formed at the access site, filtering and smoothing, manipulation of data by arithmetic techniques, use of thresholds for determining optimal imaging, blob analysis, and feature shape and moment analysis. These analyses may include analysis for a perimeter of a blob or pattern of a darker color at the access site, analysis for a centroid of the pattern, and analyses for moments of the pattern. Other software tools useful in the analysis include pattern recognition, neural networks, object segmentation, object recognition, fuzzy logic, K-nearest neighbor, quadratic classification, a polyphase filter, and linear classification. Blob is defined as a region of connected pixels. Blob analysis is the identification and study of these regions in an image. The algorithms discern pixels by their value and place them in one of two categories: the foreground (typically pixels with a non-zero value) or the background (pixels with a zero value).

A blob is a region of touching pixels. In typical applications that use blob analysis, the blob features usually calculated are area and perimeter, Feret diameter (the greatest distance possible between any two points along the boundary of a region of interest), blob shape, and location. The versatility of blob analysis tools makes them suitable for a wide variety of applications such as pick-and-place, pharmaceutical, or inspection of food for foreign matter. Since a blob is a region of touching pixels, analysis tools typically consider touching foreground pixels to be part of the same blob. Consequently, what is easily identifiable by the human eye as several distinct but touching blobs may be interpreted by software as a single blob. Furthermore, any part of a blob that is in the background pixel state because of lighting or reflection is considered as background during analysis. A reliable software package will indicate how touching blobs are defined. For example, touching pixels may be defined as adjacent pixels along a vertical or horizontal axis as pixels that are touching or may include diagonally adjacent pixels.

Machine vision programs useful for detecting and measuring the shape of the pattern are available from Matrox, Inc., Dorval, Quebec, Canada. Useful programs include the Matrox Imaging Library (MIL). These programs may be described as a "tool box" of analytical tools suitable for analyzing an array of sensory inputs, such as pixels from a digital camera, to determine the shape of an object. Other commercially available programs may also be used. Analytical tools from Matrox may be used with data from the camera and a classification scheme to estimate the nature of the pattern.

Object recognition techniques may include parametric and non-parametric techniques. These techniques may include linear classifiers, quadratic classifiers, nearest neighbor techniques, neural networks, fuzzy logic techniques, decision trees, clustering, and so forth. All these techniques may be used to interpret the optical signals and to train the system to identify the pattern of a blood leak as it grows and the pattern increasingly extends across the bandage or the patient's arm in an irregular manner. Alternatively, an infiltration will result in a pattern that grows, probably more slowly and in a more confined manner, and likely with a very different shape. Machine vision programs, using pattern recognition software as described above, including blob analysis and feature shape, may be used to recognize a shape, determine its area, determine whether it is growing over time, whether it has a color within the matching spectrum, and finally, a decision as to whether it likely to be a pool of blood atop or under the skin. Of course, if the software determines a likelihood that the pattern is blood, an alert or alarm may be given, therapy may be ceased, and a caregiver alerted, or other appropriate action taken.

For example, a nearest-neighbor technique or algorithm may be used to determine the image in a particular area by looking at the images of the "neighboring" pixels in the digital camera, charge-coupled device, or video sensor array. One of the useful features of digital device with many pixels is that each pixel is close to several other pixels. The "nearest-neighbor" technique may thus be valuable in completing the "picture" or image of a load in areas where the image is indistinct or blurred.

Neural network-type algorithms may also be very helpful in determining the classification of a particular pixel whose reading may be doubtful. The question is frequently whether the particular reading is correct or incorrect, and whether the image or color detected should be lower or higher to match the readings of other pixels near the doubtful reading. For example, a growing pool of blood might be wicked in one direction by the gauze, thus expanding the pattern for which recognition is desired. In another direction, however, an extra fold of the gauze might act as a dam and hold up blood infiltration.

Filtering by color may also be used to determine whether the pattern detected is blood. Light transmitted is detected by the video camera after the light passes through light filter 24. The filter or filters are selected to absorb light or block light of desired wavelengths, and thus to enhance the sensitivity and improve the reliability of the detection sensor and the access disconnect system. If a filter is not desired, it is also possible to perform the filtering function within the electronics and software.

In one embodiment, such a program is used to periodically update whether a pattern or pool of blood has formed, depending on the nature and extent of the pattern. The update should be reasonably frequent, such as about 1 Hz to about 10 Hz, or an update about once per second to about ten times per second, with required calculation cycle times of about 1 sec and 100 ms, respectively. In another embodiment, the update may take place about every 0.5 to 2.0 seconds, with longer calculation cycle times allowed. Other embodiments may use other time periods.

Figure 5:
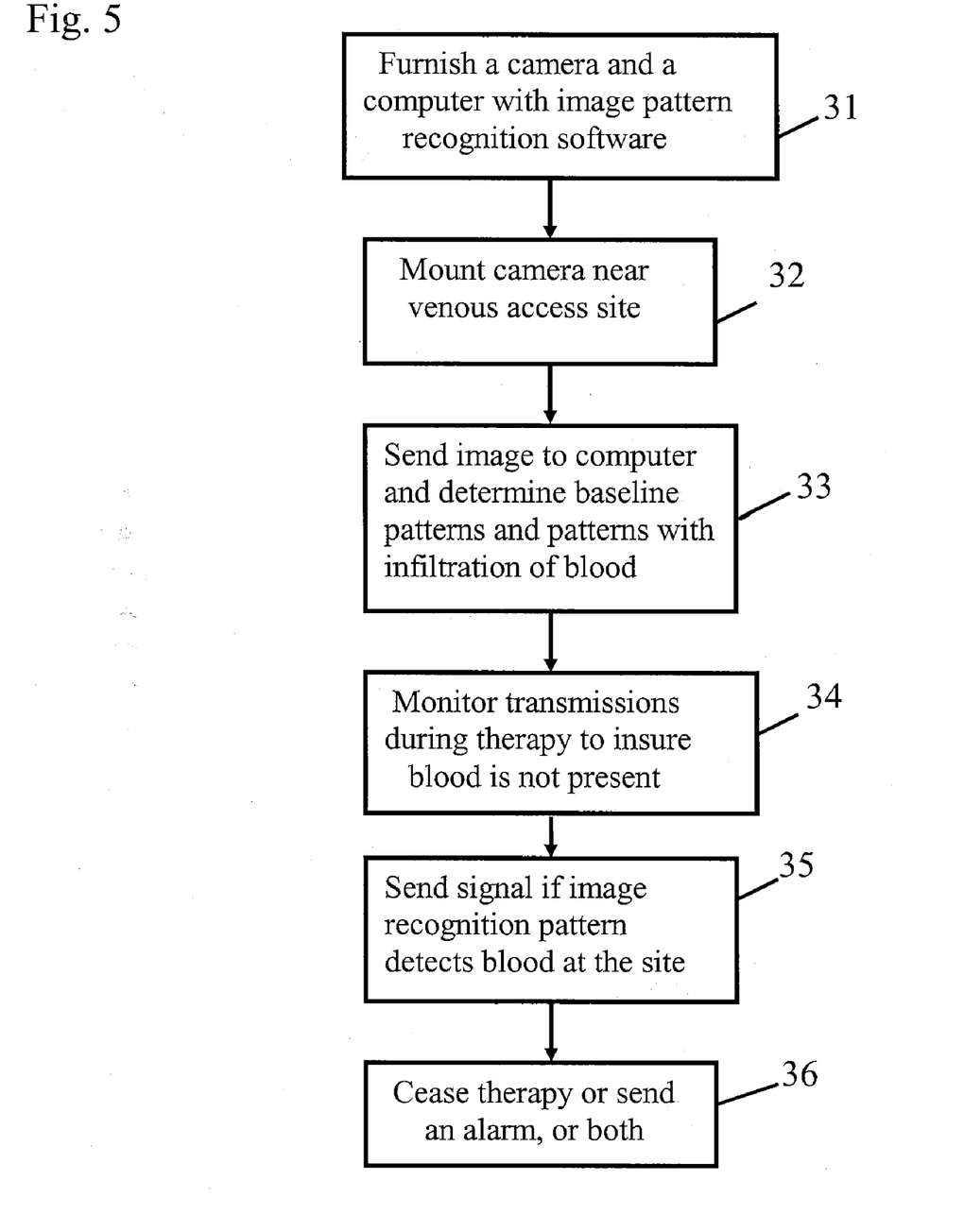
FIGS. 5-6 are flow charts depicting method embodiments.

A method for detecting blood using this equipment is also disclosed. FIG. 5 depicts a method for detecting blood using a digital video device or camera. The method includes furnishing 31 a digital video device or camera and a computer with image pattern recognition software. The device is mounted 32 near a venous access site or other area of interest. While the device may be manually mounted, for example on a tripod, it may be more useful to place the camera on a tilt-and-pan mechanism. Such systems are available commercially, such as those from Telemetrics, Mahwah, N.J., U.S.A. The movement may be controlled by a computer for the blood detection system, using a keyboard or a joystick. Such systems are available commercially, such as those sold by Panasonic Corp., Secaucus, N.J., U.S.A. The detection system may also have a dedicated monitor to more easily and accurately make the adjustment, or it may use a monitor that is part of the control system for the hemodialysis machine.

The image detected by the camera is then sent to image processing and the computer to determine 33 baseline patterns and to distinguish baseline, no-blood patterns from patterns showing blood. These patterns, or information for identifying such patterns, may then be stored in the computer or in the EEPROM as discussed above. During therapy, the patient access site is monitored 34 to see whether blood is present. It is understood that there may be small amounts of blood, such as a small amount on the access site, or a portion of the patient's vein visible to the video camera, or the blood present in the tubing lines to and from the patient. These portions of the image are programmed in as part of the baseline. The system microcontroller then sends a signal 35 if the image recognition system detects an image of blood at the site in excess of the baseline or beyond a standard for an amount of blood. The signal will then result in cessation 36 of therapy, an alarm, or other appropriate action.

Figure 6:
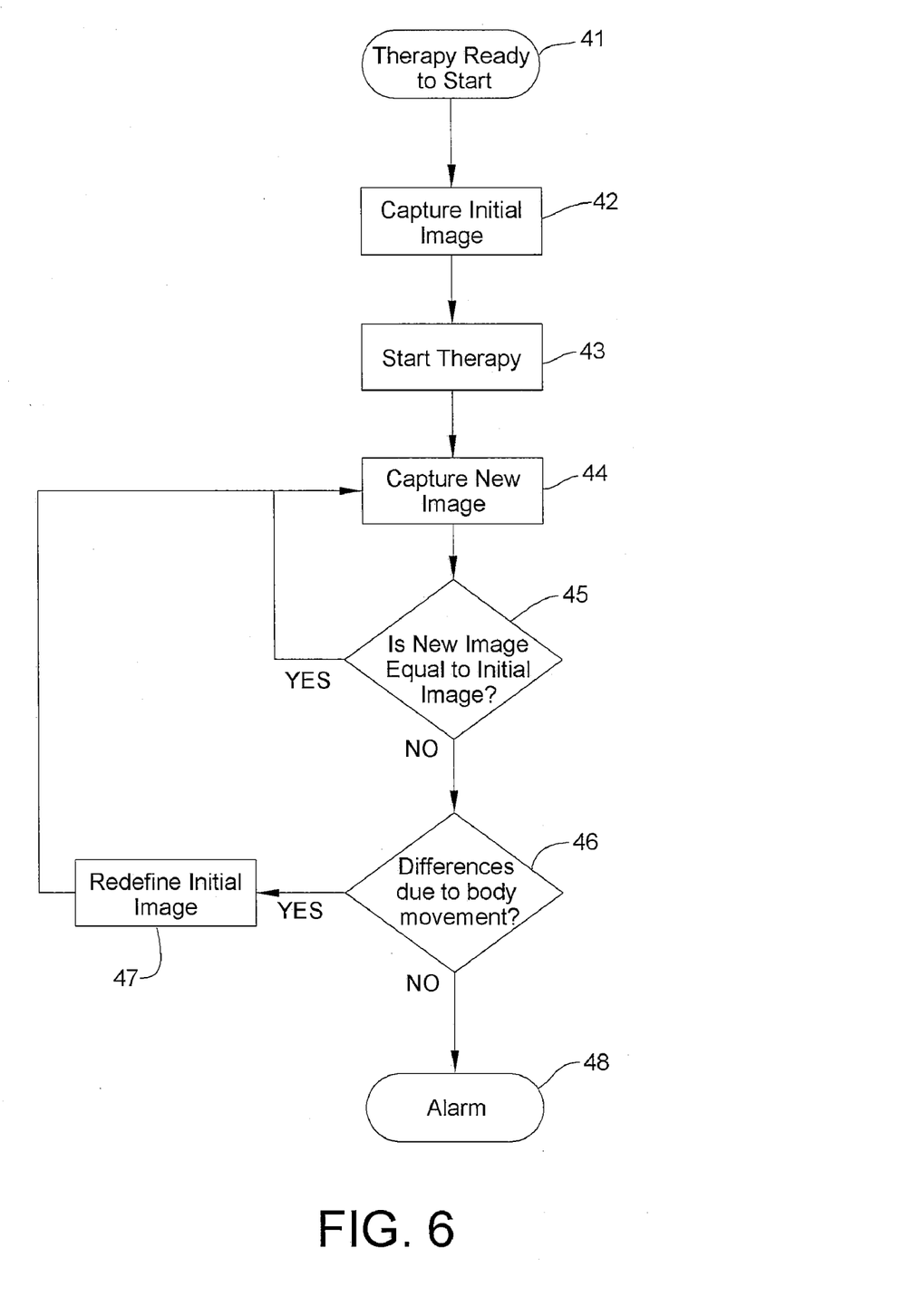

There are other ways to use the blood detector system, of which one is depicted in FIG. 6. In this method, the setups discussed above have been completed, and the detector system is 41 ready for use along with the therapy machine. The video system is turned on and the access site initial image is captured 42 and used for the baseline. Therapy is started 43 and a new image is captured periodically 44, on a rate of about 0.5 Hz to about 10 Hz, that is, at a rate from about 10 times per second to about once every 2 seconds. The image software discussed above compares each image to the baseline image to determine whether there has been a change 45. The change may be in the image itself or in the quantity of blood detected. If there is no change, the process is repeated and a new comparison is made. If there is a change in the image, the software compares the new image with previous images of an access site or the patient to determine 46 whether the difference was due to body movement of the patient. If so, then the new image is used to redefine 47 the baseline image, and the next image is taken. If the change or difference is determined as not due to body movement, but to the presence of blood, a signal may be sent or an alarm or alert sounded 48.

Most of the techniques above have been described with respect to video cameras. These techniques are also useful with infra-red images. For example, if blood leaks from the access site, the first indication may be additional heat in the area of the leak, caused by blood at body temperature leaking onto the person's arm, which will normally be at a cooler temperature. Thus, infrared imaging may also be used. The techniques described above for pattern recognition also apply to patterns formed by discrete temperature increments. For example, the temperature range may be divided into five-degree increments or three-degree increments, or even single-degree increments, for the range from 70° F. to 99° F. If a portion of the patient's arm area near the access site suddenly changes from 70° F. to a temperature that is near 90° F., it is likely that a disconnect has occurred, and action should be taken at once.

In a similar manner, low light cameras may also detect moving objects, such as a pool of blood. The same techniques discussed above with respect to pattern recognition software may also be used for the highly-amplified night vision images as well.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A method of detecting blood leakage, the method comprising:
   providing a digital video camera;
   mounting the camera to observe an extracorporeal blood processing access site;
   taking a baseline image of the access site on a patient;
   processing the baseline image with image processing software and saving data of the baseline image;
   monitoring the access site by taking additional images of the access site during an extracorporeal blood processing therapy and processing the additional images with the image processing software to detect a pattern of blood leakage under the skin of the patient; and
   sending a signal if a pattern of blood leakage under the skin of the patient is detected.

2. The method of claim 1, wherein the camera is selected from the group consisting of an infrared camera and a night vision camera.

3. The method of claim 1, wherein the signal is sent to a local output device to alert a person or to sound an alarm.

4. The method of claim 1, further comprising placing a contrasting material atop the access site.

5. The method of claim 1, further comprising processing the baseline image for color recognition of the blood and processing the additional images of the access site for color change.

6. The method of claim 1, wherein the step of monitoring includes processing the additional images for pattern recognition, shape analysis or blob analysis.

7. The method of claim 1, further comprising filtering light reaching the camera to selectively pass light with a wavelength of reflected light.

8. A method for detecting blood leakage at an access site, the method comprising:
   providing a digital video device;
   mounting the device in viewing range of the access site on a patient;
   taking a baseline image of the access site;
   processing the baseline image with pattern recognition software;
   saving data of the baseline image;
   monitoring the access site during a therapy procedure by taking additional images and processing the additional images with the pattern recognition software to detect a pattern of blood leakage under the skin of the patient; and
   sending a signal if a pattern indicative of a blood leakage under the skin of the patient is detected.

9. The method of claim 8, wherein the software uses at least one of machine vision, pattern recognition, blob analysis, and feature shape to determine blood leakage.

10. The method of claim 8, wherein the software interprets a pattern with growing edges and a temperature or color change as blood leakage.

11. The method of claim 8, wherein the software processing includes at least one technique selected from the group consisting of machine vision, pattern recognition, blob analysis, feature shape, feature moment, neural networks, object segmentation, object recognition, fuzzy logic, K-nearest neighbor, quadratic classification, a polyphase filter, and linear classification.

12. The method of claim 8, further comprising filtering images taken by the camera to enhance detecting blood.

13. The method of claim 8, wherein the baseline image includes data on colors of the image and wherein the step of monitoring includes color analysis of the additional images.

14. A system for detecting blood leakage, the system comprising:
   a digital video device suitable for mounting near an access site of a patient for extracorporeal therapeutic blood processing;
   signal processing circuitry operably connected to the digital video device;
   image processing software on a computer readable medium operably connected to the signal processing circuitry, the image processing software suitable for recognizing a pattern;
   a microcontroller in communication with the digital video device and the circuitry; and
   a communications circuit in communication with the microcontroller, wherein the digital video device is configured for monitoring the access site during an extracorporeal blood processing therapy and for sending images of the site to the signal processing circuitry, and wherein the image processing software is configured to detect a leakage of blood under the skin of the patient by recognizing a pattern or shape of a blood pool growing under the skin of the patient during the therapy.

15. The system for detecting blood leakage according to claim 14, further comprising an output device for raising an alarm or ceasing dialysis if blood is detected.

16. The system for detecting blood leakage according to claim 14, further comprising an optical filter.

17. The system for detecting blood leakage according to claim 14, wherein the software is configured to interpret infrared images as a pattern of temperatures.

18. The system for detecting blood leakage according to claim 14, wherein the image processing software is configured for recognizing patterns and shapes.

19. The system for detecting blood leakage according to claim 14, wherein the system is configured for using at least one of machine vision, pattern recognition, blob analysis, and feature shape to determine blood leakage.

20. The system for detecting blood leakage according to claim 14, further comprising a hemodialysis machine operably connected to the system for detecting blood leakage.

21. A hemodialysis machine, comprising:
   a machine for administering extracorporeal hemodialysis of blood of a patient;
   a system for detecting blood leakage during hemodialysis, the system operably connected to the machine, the system further comprising:
   a digital video camera for monitoring an access site of the patient;
   signal processing circuitry for receiving signal data from the camera;
   image processing software on a computer readable medium operably connected to the signal processing circuitry;
   a microcontroller in communication with the digital video device and the circuitry; and
   a communications circuit in communication with the microcontroller, wherein the digital video device is configured for monitoring the access site during an extracorporeal blood processing therapy and for sending images of the site to the signal processing circuitry, and wherein the image processing software is configured to detect a leakage of blood under the skin of the patient that is growing during the therapy.

22. The hemodialysis machine according to claim 21, further comprising a movable mount for the digital video camera.

23. The hemodialysis machine according to claim 21, wherein the software further comprises logic for at least one technique selected from the group consisting of machine vision, pattern recognition, blob analysis, feature shape, feature moment, neural networks, object segmentation, object recognition, fuzzy logic, K-nearest neighbor, quadratic classification, a polyphase filter, and linear classification.

24. The hemodialysis machine according to claim 21, wherein the image processing software is configured for recognizing patterns and shapes.

\* \* \* \* \*